United States Patent
Beham

(10) Patent No.: US 6,527,846 B1
(45) Date of Patent: Mar. 4, 2003

(54) GLASS-CERAMIC MATERIAL FOR DENTAL RESTORATION AND METHOD FOR PRODUCING SAME

(75) Inventor: Gerhard Beham, Triesen (LI)

(73) Assignee: Chemichl AG, Landstrasse (LI)

( * ) Notice: Subject to any disclaimer, the term of this patent is extended or adjusted under 35 U.S.C. 154(b) by 0 days.

(21) Appl. No.: 09/763,168

(22) PCT Filed: Jun. 9, 1999

(86) PCT No.: PCT/CH99/00249

§ 371 (c)(1),
(2), (4) Date: Feb. 16, 2001

(87) PCT Pub. No.: WO00/10509

PCT Pub. Date: Mar. 2, 2000

(30) Foreign Application Priority Data

Aug. 17, 1998 (CH) .............................................. 1685/98

(51) Int. Cl.[7] ........................... C03C 10/00; A61K 6/02
(52) U.S. Cl. ............................... 106/35; 501/5; 501/66; 501/70; 501/71; 501/72
(58) Field of Search ............................... 106/35; 501/5, 501/66, 70, 71, 72

(56) References Cited

U.S. PATENT DOCUMENTS 4,798,536 A    1/1989  Katz ....................... 433/212.1
5,622,551 A    4/1997  Erbe et al. ..................... 106/35
5,653,791 A    8/1997  Panzera et al. ................ 106/35
5,698,019 A   12/1997  Frank et al. ................... 106/35

FOREIGN PATENT DOCUMENTS

EP    0 272 745    6/1988
EP    0 475 528    3/1990

OTHER PUBLICATIONS

Database WPI, Section Ch, week 7833, Derwent Publications Ltd. London, GB: class L02, AN–78–59289A, XP002112378, JP 53 078220 A (Jul. 11, 1978).

*Primary Examiner*—C. Melissa Koslow
(74) *Attorney, Agent, or Firm*—Finnegan, Henderson, Farabow, Garrett & Dunner, LLP

(57) ABSTRACT

The invention relates to a glass-ceramic material for dental restoration having a high crystalline leucite content. The leucite crystals are needle- or rod-shaped, have a thickness of between 0.3 and 1.5 micrometers and are between 7.5 and 20 micrometers in length. Said glass-ceramic material is substantially semi-transparent and contains, in% by weight: between 67 and 71% $SiO_2$, between 8 and 12% $Al_2O_3$, between 3 and 5% $Na_2O$, between 8 and 10% $K_2O$, between 1 and 3% CaO, between 0.2 and 2% BaO, between 0.5 and 2% $CeO_2$, between 0.2 and 1% $TiO_2$ and between 0.5 and 2% $B_2O_3$. The above glass-ceramic material presents improved fracture strength and offers new indications for the use of full ceramic materials in dental technology, notably metal-free dental restoration.

10 Claims, 2 Drawing Sheets

GLASS-CERAMIC MATERIAL FOR DENTAL RESTORATION AND METHOD FOR PRODUCING SAME

This application is a national stage filing under 35 U.S.C. §371 of international application no. PCT/CH99/00249, filed on Jun. 9, 1999.

FIELD OF THE INVENTION

The invention relates to a glass ceramic for dental restoration and to a method for its production.

BACKGROUND OF THE INVENTION

A glass ceramic of this type is known from U.S. Pat. No. 4,798,536. This patent describes a specific porcelain material which is used as a tooth replacement material. Porcelain as a tooth replacement material has in principle been known for a long time, and is also known to be relatively susceptible to breaking. Therefore, metal substructures have generally been used in order to obtain the desired strength.

U.S. Pat. No. 4,798 536 has disclosed a porcelain material which has breaking strength properties which are such that it appears to be suitable for use as a dental material on its own.

However, it has emerged that the forces and loads which occur in the mouth may nevertheless impose loads on the material which may cause it to break.

SUMMARY OF THE INVENTION

Working on the basis of this prior art, the invention is based on the object of improving a glass ceramic of the type mentioned in the introduction in such a way that it is more resistant to breaking. A further object of the present invention is to specify a method for its production.

These objects are achieved by means of the features of claims 1 and 9, respectively.

DETAILED DESCRIPTION

Figure 1:
Figure 2:

The invention will now be described in more detail, by way of example, with reference to the enclosed diagrams, in which:

FIG. 1 shows a scanning electron microscope image, one bar on the scale representing 10 micrometers, and FIG. 2 shows an enlargement of the SEM image from FIG. 1.

A range of feldspar products, for example Canadian or Norwegian feldspar, can be used as starting materials to produce the semi-transparent ceramic, the color of which is similar to that of teeth. Other starting materials can also be used. The potassium-sodium ratio is important when selecting the feldspar. It is preferred to use potash feldspar, which in mineral form always contains sodium. The ratio of $Na_2O$ to $K_2O$ should be less than 1 to 10. The glass ceramic on which the invention is based, that is to say the end product, corresponds to the following composition, in percent by weight:

| Material | Percent by weight |
| --- | --- |
| $SiO_2$ | 67–71 |
| $Al_2O_3$ | 8–12 |
| $Na_2O$ | 3–5 |
| $K_2O$ | 8–10 |
| CaO | 1–3 |
| BaO | 0.2–2 |
| $CeO_2$ | 0.5–2 |
| $TiO_2$ | 0.2–1 |
| $B_2O_3$ | 0.5–2 |

For example, the composition may have the components in the following amounts:

| Material | Percent by weight |
| --- | --- |
| $SiO_2$ | 68–71 |
| $Al_2O_3$ | 9–11 |
| $Na_2O$ | 4–5 |
| $K_2O$ | 9–10 |
| CaO | 1.5–2.5 |
| BaO | 0.5–1.5 |
| $CeO_2$ | 0.5–1 |
| $TiO_2$ | 0.2–0.5 |
| $B_2O_3$ | 0.5–2 |

A pigment may be added to the semi-transparent material. Such a pigment may be, for example, selected from chromates, vanadinates, manganates and mixtures thereof.

The raw materials have been mixed in the form of silicates, carbonates or oxides. The resultant mixture of raw materials has been melted in a cascade crucible at approximately 1500° C. and a throughput of approximately 2 kg/h. The residence time in the crucible was approximately one hour. The melt can also be melted in a range from 1470° C. to 1550° C. and in different form.

The glass melt has then been added dropwise from the melting furnace directly into water, solidifying spontaneously to form an amorphous glass in grit form. After drying of the water-quenched glass melt, the coarse-grained glass was milled in a ball mill. As soon as the milled material stuck to the milling drum, the dry milling operation was ended. After the milling, the resultant glass powder was screened through a screen of <80 microns. The mean grain size was approximately 20 microns.

To produce dental restoration products from glass ceramic, the glass was then sintered and annealed into the desired shapes and objects. These processes are used in dental technology to produce the tooth replacement.

In an alternative procedure, the glass ceramic powder may also be dry-pressed and then converted into a solid glass ceramic object by a sintering/annealing firing operation. This procedure is advantageously used to produce semi-finished products or blanks from which an individual ceramic object, preferably for dental restoration, is produced using CAD-CAM technology.

In one embodiment of making a dental restoration product of the invention, the dental restoration product is shaped in the form of a crown or inlay on a refractory model using a slip formed from the glass powder and water, and wherein the glass powder is sintered and annealed at approximately 820° C. for a holding time of 10 minutes, or wherein the glass powder is cold-pressed in a refractory model from a plasticized glass mass and is then sintered and annealed under pressure at approximately 800 to 900 ° C.

The material produced in accordance with the above procedure is a leucite-reinforced ceramic which can be used to produce fully ceramic crowns without metal reinforcement. The leucite content of the new glass ceramic is more than 90%. This information can be found from the SEM images, since quantitative analysis is generally inaccurate. The high coefficient of thermal expansion of $19.0 * 10^{-6} K^{-1}$ also indicates a high leucite content. The literature value of the leucite is given as 20 to 22.

The crystals in U.S. Pat. No. 4,798 536 are smaller than 35 microns, preferably smaller than 5 microns, and are substantially in leaf form, with a length to width ratio of 1:1 to 1:3, and have principle dimensions in two directions between 1 and 10 microns.

In the crystals according to the present invention, a new needle-shaped, strongly matted structure has been formed. The individual crystals are needle- or column-shaped with a thickness of between 0.3 and 1.5 micrometers and have a length of between 7.5 and 20 micrometers. They are preferentially oriented in groups in a star shape starting from a nucleus as the center point, from which the leucite crystals form along star-shaped paths. When the amorphous glass is heated, the leucite crystals form in the temperature range from 800 to 900° C. Definite clouding of the originally transparent glass is visually recognizable after a holding time of even 2 minutes. The columns are preferably 0.5 to 1 micrometer thick for a length of between 8 and 12 micrometers. The ratio of length to width is at least 5:1 and may be up to 15:1. It is preferably in the region of 10:1.

Test specimens were sintered from this glass ceramic material with a high level of leucite crystals in needle form produced in situ, these specimens were sawn using a diamond saw and their three-point bending strength was determined. The sawn specimens had a bending strength of 200 MPa, and after a suitable surface treatment, such as glazing, strengths of between 300 and 350 MPa were achieved. The novel glass ceramic material therefore has an improved breaking strength and opens up new application areas for the use of solid ceramic in dental technology, in particular for metal-free restoration.

The composition of the glass now allows simultaneous annealing and sintering. The crystallization occurrs relatively spontaneously and quickly, within a few minutes. After the sintering of the glass powder, the needle-shaped crystals form in a star-shaped arrangement. The conventional two-phase production process is reduced to a single process step, in which sintering and crystallization take place simultaneously. The crystal structure in needle or fiber form which is formed increases the strength compared to previous leucite forms.

The enclosed figures show SEM images in which the glass ceramic material has a high concentration of crystal needles matted together, with a diameter of 1 micron and a length of 10 microns. The three-point bending strength of the leucite-reinforced glass ceramic achieved is approximately twice as high as with conventional leucite-reinforced ceramics.

The coefficient of thermal expansion for purely leucite crystals is approximately 20 to $22*10^{-6} K^{-1}$. With the glass ceramic according to the invention, it is possible to achieve a value of 19 to $20*10^{-6} K^{-1}$, which reflects the improved strength. The glass matrix has a coefficient which is approximately $10*10^{-6} K^{-1}$.

The prior art reveals relatively inhomogeneous leucite crystal distributions which form large surfaces and therefore also large areas for forces to attack. In the prior art, the leucite crystals are simply embedded in amorphous materials and form islands of strength in the amorphous glass phase. By contrast, the invention provides long, thin crystals which are oriented in numerous different directions and which, as can be seen from the drawings, do not simply form islands of strength in the amorphous glass phase, but rather constitute strong, cohesive structures around the nucleus at the center of the star, in which material fractures in the microfracture range are reliably halted even after short distances.

What is claimed is:

1. A glass ceramic having a high crystalline leucite content, the leucite crystals being in needle or column form, having a thickness of from 0.3 to 1.5 micrometers and having a length of from 7.5 to 20 micrometers and the glass ceramic substantially being a semi-transparent material which comprises:

| Material | Percent by weight |
| --- | --- |
| $SiO_2$ | 67–71 |
| $Al_2O_3$ | 8–12 |
| $Na_2O$ | 3–5 |
| $K_2O$ | 8–10 |
| CaO | 1–3 |
| BaO | 0.2–2 |
| $CeO_2$ | 0.5–2 |
| $TiO_2$ | 0.2–1 |
| $B_2O_3$ | 0.5–2. |

2. The glass ceramic as claimed in claim 1, wherein the needles or columns which form the leucite crystals form groups of needles or columns.

3. The glass ceramic as claimed in claim 2, wherein the groups of needles or columns which form the leucite crystals are arranged substantially in a star shape, starting from a center point.

4. The glass ceramic as claimed in claim 1, wherein the leucite crystals have a thickness of approximately 0.5 to 1 micrometer for a length of from 8 to 12 micrometers.

5. The glass ceramic as claimed in claim 1, wherein the semi-transparent material comprises.

| Material | Percent by weight |
| --- | --- |
| $SiO_2$ | 68–71 |
| $Al_2O_3$ | 9–11 |
| $Na_2O$ | 4–5 |
| $K_2O$ | 9–10 |
| CaO | 1.5–2.5 |
| BaO | 0.5–1.5 |
| $CeO_2$ | 0.5–1 |
| $TiO_2$ | 0.2–0.5 |
| $B_2O_3$ | 0.5–2 |

6. The glass ceramic as claimed in claim 1, wherein the semi-transparent material of the glass ceramic further comprises a pigment.

7. The glass ceramic as claimed in claim 6, wherein the pigment is selected from the group consisting of the chromates, vanadinates, manganates and mixtures thereof.

8. The glass ceramic as claimed in claim 1, wherein its coefficient of thermal expansion is approximately $19 \cdot 10^{-6} K^{-1}$.

9. A method of producing a dental restoration product comprising a glass ceramic as claimed in claim 1, which comprises:

a) mixing silicates, carbonates, or oxides to form a composition which has, after the subsequent melting operation, the composition of the semi-transparent glass ceramic, b) melting the mixture in a cascade crucible at approximately 1 500° C., c) adding the molten glass from the melting furnace dropwise directly into water to solidify the glass material, d) drying the glass material, e) dry milling the glass material to produce a glass powder, and f) sintering the glass powder into the desired shape or object and at the same time annealing the glass powder, or dry-pressing the glass powder and converting it into a solid glass ceramic object by a sintering/annealing firing operation.

10. The method as claimed in claim 9, wherein the dental restoration product is shaped in the form of a crown or inlay on a refractory model using a slip formed from the glass powder and water, and wherein the glass powder is sintered and annealed at approximately 820° C. for a holding time of 10 minutes, or wherein the glass powder is cold-pressed in a refractory model from a plasticized glass mass and is then sintered and annealed under pressure at approximately 800 to 900° C.

* * * * *